US006555227B2

(12) United States Patent
Sprenger et al.

(10) Patent No.: US 6,555,227 B2
(45) Date of Patent: Apr. 29, 2003

(54) LATENT COMBINATION COMPOUNDS AND LATENT AMMONIUM SALTS COMPRISING EPOXIDE RESIN CURING AGENTS AND FLAME-PROTECTION AGENTS AS WELL AS EPOXIDE RESIN SYSTEMS AND PRODUCTS PREPARED FROM THEM

(75) Inventors: Stephan Sprenger, Oststeinbek (DE); Rainer Utz, Escheburg (DE); Michael Ciesielski, Merseburg (DE); Manfred Doering, Dorndorf-Steudnitz (DE)

(73) Assignee: Schill & Seilacher (GmbH & Co.), Hamburg (DE)

( * ) Notice: Subject to any disclaimer, the term of this patent is extended or adjusted under 35 U.S.C. 154(b) by 0 days.

(21) Appl. No.: 09/776,273

(22) Filed: Feb. 2, 2001

(65) Prior Publication Data

US 2001/0014706 A1 Aug. 16, 2001

(30) Foreign Application Priority Data

Feb. 9, 2000 (DE) ......................................... 100 06 592

(51) Int. Cl.$^7$ ........................... B32B 27/38; B05D 3/02; C08L 63/00; C07F 9/02
(52) U.S. Cl. ....................... 428/413; 428/901; 523/400; 523/451; 523/452; 427/96; 427/386; 564/12; 564/15
(58) Field of Search ........................... 252/609; 564/12, 564/15; 528/86, 87, 116, 118; 523/400, 451, 452; 428/413, 901; 427/96, 386

(56) References Cited

U.S. PATENT DOCUMENTS

| 3,632,427 A | 1/1972 | Green |
| 3,635,894 A | 1/1972 | Dowbenko et al. |
| 3,642,698 A | 2/1972 | Green |
| 3,678,007 A | 7/1972 | Dowbenko et al. |
| 6,228,912 B1 * | 5/2001 | Campbell et al. ............ 524/100 |

FOREIGN PATENT DOCUMENTS

| DE | 43 08 184 | 3/1993 |
| DE | 44 47 277 | 12/1994 |
| EP | 0 589 166 | 7/1993 |
| EP | 0 589 167 | 7/1993 |
| EP | 0 806 429 | 5/1997 |

OTHER PUBLICATIONS

Nachev: CAPLUS Abstracts/Tetrahedron Journal (1991)/ISSN 0040–4020.*
Nachev: CAPLUS Abstracts/Bull.Chem.Soc.Jpn. Journal (1988)/ISSN 0009–2673.*

* cited by examiner

Primary Examiner—Robert Dawson
Assistant Examiner—Michael J Feely
(74) Attorney, Agent, or Firm—Collard & Roe, P.C.

(57) ABSTRACT

Combination compounds from curing agents/accelerators and flame-protection agents for the latent curing/acceleration of epoxide resin systems and their endowment with flame-retarding properties, the epoxide resin systems being able to be thermally cured, as well as the products prepared from the epoxide resin systems.

35 Claims, 3 Drawing Sheets

LATENT COMBINATION COMPOUNDS AND LATENT AMMONIUM SALTS COMPRISING EPOXIDE RESIN CURING AGENTS AND FLAME-PROTECTION AGENTS AS WELL AS EPOXIDE RESIN SYSTEMS AND PRODUCTS PREPARED FROM THEM

BACKGROUND OF THE INVENTION

1. Field of the Invention

The invention relates to latent combination compounds comprising epoxide resin curing agents and flame-protection agents. Furthermore, it relates to a process for reacting these latent combination compounds with water and/or mono- or polyhydric hydroxy compounds, and the latent ammonium salts formed during this reaction. Selected latent ammonium salts can be obtained according to an alternatively presented process. The latent combination compounds and latent ammonium salts can be used in the preparation of single-component resin systems, and moulded bodies and coatings with flame-retarding properties obtainable from them, in heat-curable single-component epoxide resin adhesives and in resin-injection processes. The invention furthermore covers prepregs and composite materials as well as printed wiring boards.

2. The Prior Art

There is a demand for epoxide resin systems which can be used in resin-injection processes, and which cure completely at as low as possible a defined temperature, have excellent material properties and are toxicologically harmless in case of fire. The known epoxide resin systems are not satisfactory in this respect, in particular problems arise during storage, as the cured systems do not have the desired mechanical properties and are not toxicologically harmless in case of fire.

Currently, only a few epoxide resin systems are known which can be used in resin-injection processes. In the case of Ciba-Geigy's RTM6 system, curing takes place at too high a temperature (180° C.) over too long a period (2 hours). A single-component epoxide resin system based on a diglycidyl ether of fluorene bisphenol from 3M is known. Although this system has good fracture mechanics values, it also cures only at 180° C. Bayer AG supplies under the trade name Blendur® an epoxiisocyanurate resin, based on diphenylmethane diisocyanate, which offers the possibility of curing at different temperatures. Through a secondary curing, again at too high a temperature (200° C.), the corresponding properties can then be achieved.

Low-temperature-curing epoxide resin systems (curing at approx. −100° C.) with a sufficiently high glass transition temperature ($T_g$ approx. 200° C.) can be obtained if a highly exothermic polymerization is achieved. This is facilitated above all by anionic homopolymerization of the epoxide resins. Particularly good results are obtained when the polymerization starters, often called accelerators in epoxide resin chemistry, are released rapidly or suddenly. This principle is called latent acceleration and is carried out in single-component resins. In epoxide resin chemistry, these accelerators are deactivated by mechanical encapsulation or through the formation of chelate complexes. By increasing the temperature, the actual accelerator substances are released again. It is decisive in particular for use in resin-injection processes that this release occurs extremely abruptly. This is an essential precondition if the resin systems are to have good flow properties during processing at increased temperature (60 to 800° C.) but cure rapidly after a slight further temperature increase (to say 100° C.).

It is known to the person skilled in the art that the terms curing agent and accelerator are not clearly distinguishable from each other in epoxide resin chemistry; above all, the substances which are added to epoxide resin systems cannot be allocated either a curing or an acceleration effect. Both terms, "curing agent" and "accelerator", are therefore used when describing this invention in order to express the capacity of the presented substances to cure any epoxide resin system or accelerate curing.

The known single-component resins which can be latently accelerated contain Lewis adducts of tertiary amines and do not fulfil the requirements. They must be stored at low temperatures and accelerate the polymerization unevenly so that a secondary tempering is required after the actual polymerization.

The documents U.S. Pat. No. 3,632,427, U.S. Pat. No. 3,642,698, U.S. Pat. No. 3,635,894 and U.S. Pat. No. 3,678,007 disclosed salts of imidazoles with mineral acids. EP 0 589 166 B1 and EP 0 589 167 B1 disclose the preparation of transition metal/heterocycle complexes which are proposed as latent polymerization catalysts for epoxide resins. The compounds mentioned are however solids which must be dissolved in solvents and their use in single-component resins, their use in resin-injection processes and in composite materials is ruled out as separation leads to unavoidable problems which impair the mechanical properties of the epoxide resin material and product.

For high-performance applications, additional modification agents (modifiers) are required in order to satisfy special requirements in terms of physical and material properties. This involves above all an improvement in elasticity (NBR modifiers) and behaviour in fire (FST modifiers).

Modern epoxide resins as well as products prepared from them must above all have flame protection. The state of the art in the case of flame protection of epoxide resins is the use of non-reactive flame protection agents such as aluminium hydroxide, magnesium hydroxide, ammonium polyphosphate or red phosphorus in the case of casting compounds and coatings. They are economical and toxicologically harmless. To achieve sufficient flame protection however, relatively large amounts must be added. As these flame protection agents do behave like non-reactive fillers and the mechanical properties are clearly impaired, they are not used in composite materials. Furthermore, they are not suitable for resin-injection processes as the fabric to be impregnated acts as a filter on the flame protection agent. The state of the art in the case of composites is the use of epoxide resins which have been reacted with tetrabromobisphenol A. Antimony trioxide is also often used as a synergist. In case of fire, however, brominated dioxins can form. In addition, the scene of the fire is contaminated with carcinogenic antimony fly ash and highly corrosive acids.

Flame-protection agents which can be reactively incorporated into epoxide resin are known from DE 44 47 277 A1, DE 43 08 184 A1 and EP 0 806 429 A2. Epoxide resin systems to which these flame-protection agents have been added are however unsatisfactory as regards their processing properties, above all pre-reacted epoxide resins are moisture-sensitive and not storage-stable.

SUMMARY OF THE INVENTION

The object of the present invention is therefore to provide single-component epoxide resin systems for manufacturing products given flame-retarding properties, with which the simple selection of a particular desired curing temperature must be possible. The epoxide resin systems are themselves to display excellent storage-stability, above all long-term storage-stability and be able to be used in resin-injection processes. The novel epoxide resin materials obtained by curing are to have excellent mechanical properties, e.g. fracture resistance and low brittleness, and simultaneously have excellent flame-protection properties without being toxicologically harmful in case of fire.

It was surprisingly found that this object is achieved by novel chemical compounds.

The invention relates inter alia to a group of phosphinic acid amides for which the term "latent combination compounds" is also used in the following, on the other hand a group of ammonium phosphinates which are also called "latent ammonium salts". Common to the presented chemical compounds according to the invention is that they are capable, upon a temperature increase, of curing the epoxide resin system to which they have been added, i.e. they are latent curing agents/accelerators; simultaneously, they facilitate the flame-proofing of the epoxide resin and of the products prepared from it.

BRIEF DESCRIPTION OF THE DRAWINGS

FIG. 1 shows reactions of a substance (PD 3710) which according to the terms used later shows the ring-closed form (intramolecular ester) of a derivative of 4-hydroxy-butane-1 phosphinic acid.

If the reaction is carried out with tertiary amine and water, ring-opening can take place accompanied by the formation of an ammonium phosphinate 1-IIb (latent ammonium salt). If the reaction of PD 3710 takes place with a secondary amine, a labile phosphinic acid amide (latent combination compound) 1-I can form, the possible decomposition of which to 1-III and 1-IIa will later be explained in more detail.

Figure 1:
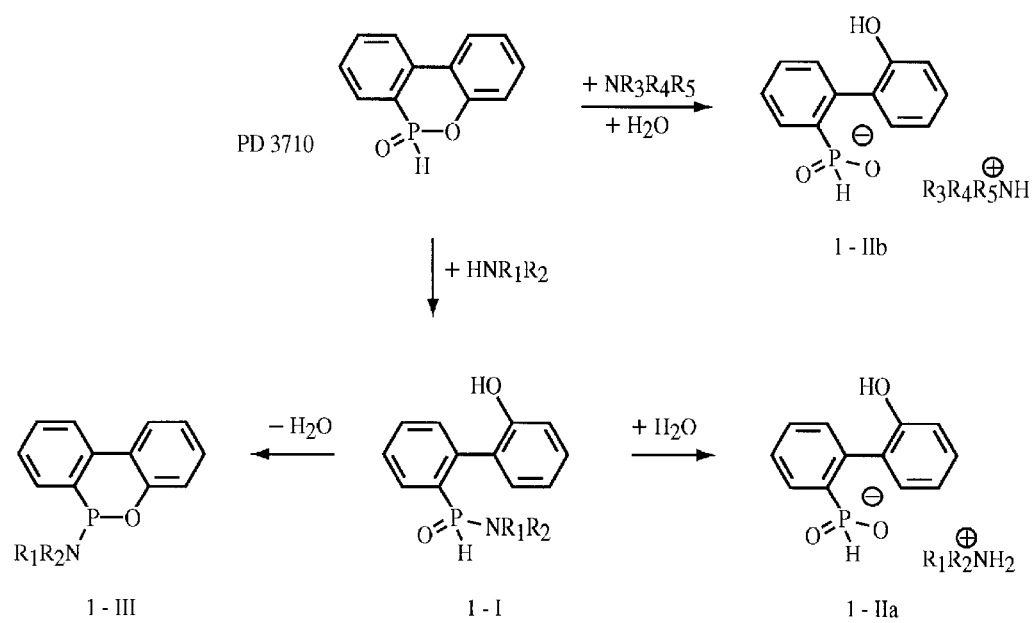
FIGS. 1–3 show a few chemical reactions which illustrate in particular the processes and compounds described later.
Figure 2:
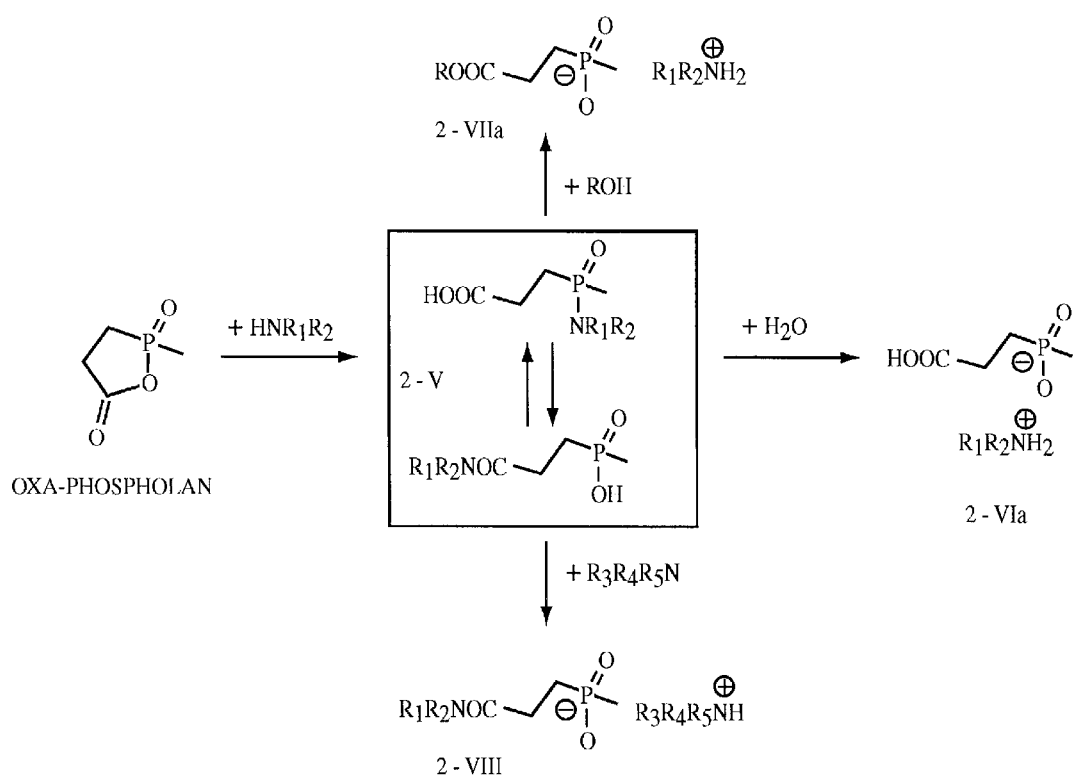

FIG. 2 shows possible reactions of a derivative of phospholan (oxa-phospholan). During the reaction with a secondary amine, the chemical equilibrium 2-V can form (the above compound again represents a latent combination compound), alcoholysis leading 2-VIIa, hydrolysis producing 2-VIa, whilst the reaction with a tertiary amine produces 2-VII. The compounds 2-VIa, 2-VIIa and 2-VIII are latent ammonium salts within the meaning of the terminology used in the description of the present invention.

Figure 3:
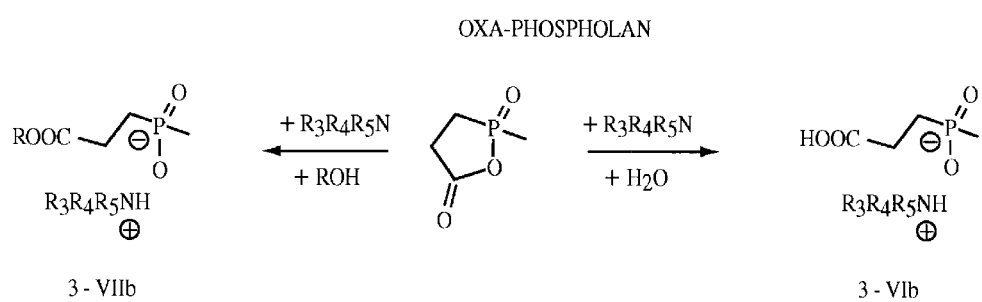

FIG. 3 shows possible reactions of a derivative of phospholan (oxa-phospholan) during the reaction with a tertiary amine. Regardless of the co-component—often called component (c) in the following—ring-opening of the oxa-phospholan occur: if component (c) is an alcohol, esterification takes place (3-VIIb), if component (c) is water, the free carboxylic acid is present under certain circumstances (3-VIb). Both 3 VIb and 3 VIIb are ammonium phosphinates (latent ammonium salts).

DETAILED DESCRIPTION OF PREFERRED EMBODIMENTS

In the description of the present invention, for simplicity's sake, $R^0$ denotes hydrogen or a linear or branched, saturated or unsaturated hydrocarbon group with 1 to 100 carbon atoms which can optionally contain one or more heteroatoms chosen from oxygen, nitrogen, sulphur, phosphorus, silicon and halogen. In the hydrocarbon group, the number of heteroatoms is preferably limited to 3 heteroatoms per 10 carbon atoms, preferably 1 hetero atom per 10 carbon atoms. Particularly preferred are hydrocarbon groups which contain 0 to 2 hetero atoms.

I. Latent Combination Compounds

The above-mentioned object is achieved by latent combination compounds corresponding to formula I

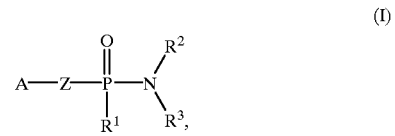

in which $R^1$ has the meaning given for $R^0$, $R^2$ and $R^3$, independently of each other, have the meaning given for $R^0$, and $R^2$ and $R^3$ can be linked accompanied by the formation of a cycle or several cycles, A is selected from the group consisting of OH and COX, in which X is selected from the group consisting of OH, $NH_2$, $NHR^4$, $NR^bR^c$, OR or $O^-M^+$, and $R^a$ to $R^d$, independently of each other, have the meaning given for $R^0$, and $R^b$ and $R^c$ can be linked accompanied by the formation of a cycle or several cycles and $M^+$ is any metal cation, and Z denotes a divalent linear or branched, saturated or unsaturated hydrocarbon chain with 2 to 100 carbon atoms which can optionally contain one or more heteroatoms selected from oxygen, nitrogen, sulphur, phosphorus, silicon and halogen.

The latent combination compounds according to the invention are to be understood in formal terms as derivatives of phosphinic acid amides and, depending on whether $R^1$ is hydrogen or is not hydrogen, singly or doubly phosphorus-substituted phosphinic acid amides.

The groups represented by a) A—Z and b) $R^1$ in formula I are preferably different.

In group Z, the number of heteroatoms can be limited to 3 hetero-atoms per 10 carbon atoms, preferably 1 hetero atom per 10 carbon atoms. Particularly preferred are groups Z which contain 0 to 2 hetero atoms. In another preferred version, the group Z has no hetero atom in the chain.

In general, the group $R^1$ is preferably not a pure aryl group, e.g. it is not a phenyl group $C_6H$, or an aryl group derived from a phenyl group without any aliphatic character. Preferably, the group $R^1$ is selected from those known from EP 0 806 429 A2 as well as methyl and hydrogen.

$R^1$ can be for example hydrogen or an aliphatic, alicyclic or aromatic hydrocarbon group. In the hydrocarbon group, combinations such as alkylaryl or arylalkyl radicals are also to be considered and it can moreover contain one or more heteroatoms selected from oxygen, nitrogen, sulphur, phosphorus, silicon and halogen. Preferably, the hydrocarbon group is an aliphatic hydrocarbon group, for example methyl. In another aspect, the hydrocarbon group contains at least one functional group selected from epoxy groups, α,β-diol groups and carboxylic acid, carboxylic acid ester and carboxylic acid anhydride groups. Particularly preferably, $R^1$ is selected from hydrogen, methyl and hydrocarbon groups which have at least one epoxy function. Functionalized hydrocarbon groups which are bound to a phosphorus atom of a phosphinic acid derivative are for example known from EP 0 806 429 A2.

The preferred latent combination compounds according to the invention can be divided into two classes:

A) Latent combination compound according to formula I in which A equals OH. Preferably, Z contains 4 carbon atoms in the chain and contains no heteroatoms in the chain. Particularly preferably, z equals but-1,4-diyl (1,4-butylene) or its derivatives.

For example, Z is selected from biphen-2,2'-diyl and derivative of biphen-2,2'-diyl. These latent combination compounds are derived from the amides of 4-hydroxy-butane-1-phosphinic acid, particularly preferably from the amides of the fused benzene ring derivatives of 4-hydroxy-butane-1-phosphinic acid. These fused benzene ring derivatives of 4-hydroxy-butane-1-phosphinic acid, e.g. those which correspond to 9,10-dihydro-9-oxa-10-phospha-phenanthrene-10-oxide in its ring-open form, are described in EP 0 806 429 A2.

In a particularly preferred aspect, the group $R^1$ has at least one epoxy function. Regardless of this, $R^1$ is preferably different from the group represented by A–Z.

(B) Latent combination compound according to formula I in which A equals COOH. Z can be linear or branched and alkane-$(\alpha,\beta)$-diyl or arylalkane-$(\alpha,\beta)$-diyl. In a particularly preferred version, Z is linear or branched and an alkane-$(\alpha,\beta)$-diyl, e.g. —$CH_2CH_2$—, and $R^1$ equals methyl or hydrogen.

Regardless of versions A) and B), $R^2$ is preferably not hydrogen; particularly preferably, both $R^2$ and $R^3$ are not hydrogen. The latter is the case e.g. in those phosphinic acid amides according to formula I which contain an imidazole-1-yl group as $NR^2R^3$ group.

Examples of $R^2$ and $R^3$ are hydrogen or a hydrocarbon group which optionally contains one or more heteroatoms selected from oxygen, nitrogen, sulphur, phosphorus, silicon or halogen.

The hydrocarbon groups can be linear or branched alkyl groups, cycloalkyl groups, aryl groups, alkylaryl groups or arylalkyl groups, and combinations of the above-named possibilities are also to be considered. The hydrocarbon groups $R^2$ and $R^3$ can be linked to each other to form saturated or unsaturated cycles, five-membered and six-membered rings being preferred. Particularly preferred is the linking of R and R3 to form five- or six-membered rings, further heteroatoms being able to be contained in these rings. The nitrogen can be incorporated during the linking to form cycles.

If $R^2$ and $R^3$ are linked to form a cycle, the function $NR^2R^3$ can be derived for example from imidazole, 2-methylimidazole and 2-ethyl-4-methylimidazole.

As will be explained later, the latent combination compound according to the invention can be advantageously used in its form corresponding to formula I in epoxide resin pre-products (e.g. in single-component resin systems) or finished epoxide resin products, e.g. epoxide resin adhesives.

It is however not necessarily prescribed that the latent combination compounds according to the invention must be isolated in substance in their form corresponding to formula I. In the preparation of substances which are covered by formula I, their isolation can be dispensed with, thus they can be further processed in situ. This is by way of example, but not exclusively, the case when the latent combination compound is not to be used per se.

For example, solutions of the latent combination compounds sometimes decompose at room temperature. Thus a (labile) latent combination compound which in formal terms comes under formula I, which can form through reaction of a ring-closed phosphorus-containing compound of formula XV ($R^{10}$ to $R^{18}$ equals hydrogen) with a primary ($H_2NR$) or secondary (HNRR') aliphatic amine (this process is a component of the present invention), will decompose in solution to form a) 50 mol-% of a compound which is derived from formula XV by the loss without replacement of the exo-oxygen atom at the phosphorus and replacement of the group $R^{18}$ by the amino group (HNR or NRR') (this partial reaction proceeds accompanied by splitting-off of water), and b) 50 mol-% of a compound which results from the addition of water to the labile latent combination compound. The compound resulting from the addition of water corresponds to the ring-opened form XXI ($R^{18}$ equals H), that is the ammonium phosphinate derived from the primary or secondary amine by protonation. The present invention also relates, as described in the following, to such ammonium phosphinates (latent ammonium salts).

II. Latent Ammonium Salts

The invention also relates to a process in which the latent combination compound according to formula I is reacted with at least one reagent, the P—N bond of the latent combination compound being hydrolytically split, as well as the latent ammonium salts obtainable through the hydrolysis process.

According to a first possible aspect, the reagent comprises water.

According to a further aspect, a latent combination compound in which A equals COOH is reacted with at least one reagent which comprises at least one compound selected from water and mono- or polyhydric hydroxy compounds.

During the reaction of the latent combination compound with water, in a first reaction step there is always a splitting-up of the P—N bond shown in formula I, and an ammonium salt of the corresponding phosphinic acid is formed.

This latent ammonium salt can optionally be isolated, if desired.

Thus the term latent ammonium salt here includes on the one hand an ammonium phosphinate resulting from formula I, the phosphinate-phosphorus atom being either mono-substituted (when $R^1$ equals hydrogen) or disubstituted (when $R^1$ is not hydrogen).

The comments regarding the ammonium cation are not intended to mean that the ammonium cation in the latent ammonium salt must not comprise any species other than $[H_2NR^2R^3]^+$. If e.g. the reagent with which the latent combination compound according to the invention is reacted comprises, in addition to water, one or more of the nitrogen-containing compounds mentioned later as designated curing agents or accelerators, which also include tertiary amines, then the term ammonium cation also includes these nitrogen-containing compounds.

The ammonium cation of the latent ammonium salt is derived from $NR^2R^3$, is therefore $[H_2NR^2R^3]^+$, the ammonium cation not being $NH_4^+$ in a first preferred version, i.e. at least one of the groups $R^2$ or $R^3$ is to be different from hydrogen. In another preferred version, the term ammonium cation includes the $NH_4^+$ and at least a) a further ammonium cation which is not $NH_4^+$ and/or b) one of the nitrogen-containing compounds mentioned later.

In addition, the details given for $R^1$, $R^2$, $R^3$, A, Z and A—Z for the latent combination compound according to the invention are valid for the latent ammonium salt.

For the ammonium cations, it is preferable that—regardless of the versions A) and B) of the phosphinate anions discussed in the following—$R^2$ is not hydrogen, particularly preferably both $R^2$ and $R^3$ are not hydrogen, this is the case e.g. when the ammonium cation is derived from an imidazole-1-yl group.

Preferred ammonium cations are the protonated forms of imidazole, 2-methylimidazole and 2-ethyl-4-methylimidazole, the ammonium cations including those which result from protonation of the nitrogen atom in formula I, the preferred versions of the radicals $R^2$ and $R^3$ being listed above.

The preferred phosphinate anions of the latent ammonium salts according to the invention can, regardless of the ammonium cations, be divided into two classes by analogy with the statements made for the latent combination compounds:

A) phosphinate cations [(A—Z) ($R^1$)P(O)O]$^-$, A equalling OH. Preferably, Z contains 4 carbon atoms in the chain and contains no heteroatoms in the chain. Particularly preferably, Z equals but-1,4-diyl or its derivatives.

For example, Z is selected from biphen-2,2'-diyl and derivative of biphen-2,2'-diyl. These phosphinate cations are derived from 4-hydroxy-butane-1 phosphinic acid, particularly preferably from the fused benzene ring derivatives of 4-hydroxy-butane-1 phosphinic acid, as described in EP 0 806 429 A2. In a particularly preferred version, the group $R^1$ has at least one epoxy function. Regardless of this, $R^1$ is preferably different from the group represented by A—Z.

B) phosphinate cations [(A—Z) ($R^1$)P(O)O]$^-$, A equalling COOH. Z is linear or branched and alkane-($\alpha,\beta$)-diyl or arylalkane-($\alpha,\beta$)-diyl, e.g. —CH$_2$CH$_2$—, and $R^1$ equals methyl. These phosphinate cations are e.g. the ($R^1$ derivatives of) 2-hydroxycarbonyl-ethyl phosphinates [(HOOCCH$_2$CH$_2$) ($R^1$) P(O)O]$^-$.

If a latent combination compound is used in the process in which A equals COOH, the reagent is defined in that it comprises at least one compound selected from water and mono- or polyhydric hydroxy compounds. The reagent therefore need not necessarily contain water when A equals COOH. For example, in this aspect in a first reaction step, COOH of the latent combination compound according to the invention is esterified with at least one mono- or polyhydric hydroxy compound. This reaction procedure is preferred (cf. also examples 1–3). The water released by the esterification then reacts with the P—N bond in the latent combination compound, which likewise produces an ammonium phosphinate. These ammonium salts, the formation of which is brought about by an esterification, also achieve the object according to the invention and are also covered by the term latent ammonium salt. Preferred mono- or polyhydric hydroxy compounds are mono- and polyhydric, linear and branched, aliphatic, arylaliphatic and aromatic alcohols and phenols, in particular mono- or polyhydric alcohols and phenols. Phenol itself is a possible hydroxy compound. As polyhydric phenols, there are to be named here by way of example: resorcin, hydroquinone, 2,2-bis-(4-hydroxyphenyl)-propane (bisphenol A), isomer mixtures of dihydroxydiphenylmethane (bisphenol F), 4,4'-dihydroxydiphenylcyclohexane, 4,4'-dihydroxy-3,3'-dimethyldiphenyl-propane, 4,4'-dihydroxydiphenyl, 4,4'-dihydroxybenzophenone, bis(4-hydroxyphenyl)-1,1-ethane, bis-(4-hydroxyphenyl)-1,1'-isobutane, bis-(4-hydroxy-tert-butylphenyl)-2,2-propane, bis-(2-hydroxynaphthyl)-methane, 1,5-dihydroxynaphthalene, tris-(4-hydroxyphenyl)-methane, bis-(4-hydroxyphenyl)-1,1'-ether, bisphenol A and bisphenol F being particularly preferred.

Naturally, monohydric aliphatic alcohols are suitable, for example methanol, ethanol, as well as the isomeric (iso, tert., sec, n) propanols, butanols, pentanols and hexanols. Polyhydric aliphatic alcohols are also suitable as a hydroxy compound. There may be named as examples of such polyhydric alcohols 1,4-butanediol, 1,6-hexanediol, poly-alkylene glycols, glycerol, trimethylolpropane, bis-(4-hydroxycyclohexyl)-2,2-propane, 1,2-ethylene glycol, 1,2-propylene glycol and pentaerythritol.

The term latent ammonium salt also covers those ammonium salts the formation of which is initiated by the esterification of a polyhydric alcohol and which contain phosphinate units linked via the alcohol group (see example 3).

If the water used (or, if A equals COOH and an esterification takes place, the water formed during the esterification) reacts in the first reaction step at a position other than the P—N bond without the P—N bond being hydrolytically split, more water is preferably added until the P—N bond is split.

Furthermore, rearrangement of the latent ammonium salt may occur. For example, the ammonium cation can react with group A if group A equals COX, the amide being formed and accordingly a different salt of the phosphinate anion being present in formal terms. If X equals O$^-$M$^+$, then the phosphinate is present as the metal salt in formal terms after amide formation and can be transformed into other salts with different cations. In diagram 2, another of these rearrangement reactions is shown: in the ammonium phosphinate 2-VIII, the ammonium cation is not derived from the amine (secondary in this case) with which the oxa-phospholan has been converted to 2-V, but from an amine (tertiary in this case) which has been introduced later. These further rearrangement products are also covered by the term latent ammonium salt.

III. Process for Preparing Latent Combination Compounds and/or Latent Ammonium Salts It was furthermore surprisingly found that the preferred latent combination compounds and latent ammonium salts can be particularly easily prepared by reacting at least one phosphorus-containing compound (a) selected from i) derivatives of 4-hydroxy-butane-1-phosphinic acid and/ or its intramolecular ester corresponding to one of formulae X to XXI

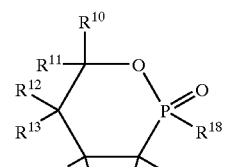

X

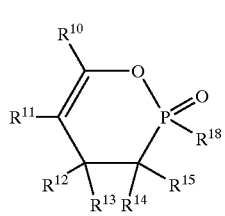

XI

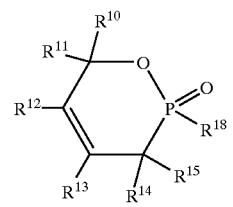
XII
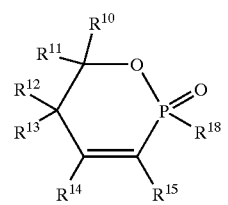
XIII
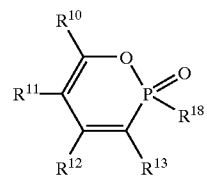
XIV
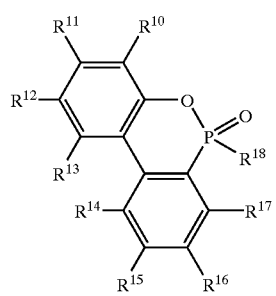
XV
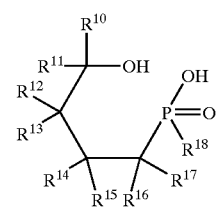
XVI
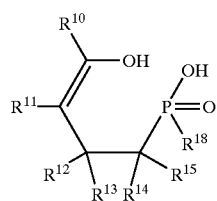
XVII
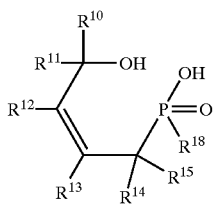
XVIII
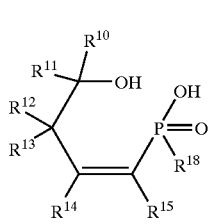
XIX
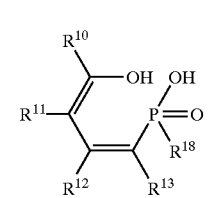
XX
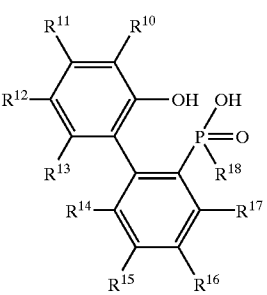
XXI
in which $R^{10}$ to $R^{18}$, independently of each other, have the meaning given for $R^0$, two of more of $R^{10}$ to $R^{17}$ being able to be linked accompanied by the formation of a cycle or several cycles, and
ii) derivatives of phospholan according to one of formulae XXX to XXXIII
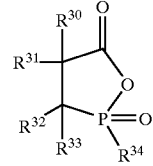
XXX
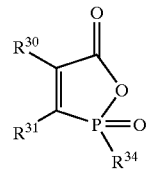
XXXI
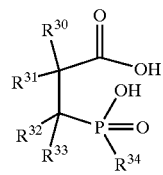
XXXII -continued

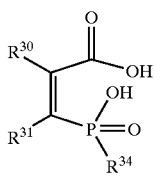

XXXIII in which $R^{30}$ to $R^{34}$, independently of each other, have the meaning given for $R^0$ and one or more of $R^{30}$ to $R^{33}$ can be linked accompanied by the formation of a cycle or several cycles, with a component (b) which comprises a nitrogen-containing compound. The precise conditions under which the process according to the invention proceeds are explained in the following.

The latent combination compounds and latent ammonium salts obtainable through the process according to the invention of the reaction of components (a), (b) and optionally (c) represent preferred versions of the latent combination compounds and latent ammonium salts according to the invention named at the outset.

Preferably, no phosphinic acid amide (latent combination compound) is formed during the process, but the reaction leads to a latent ammonium salt without the P—N bond shown in formula I.

Preferred components (a) are the phosphorus-containing compounds known from i) EP 0 806 429 A2 or ii) DE 44 47 277 A1.

Examples of $R^{18}$ and $R^{34}$ are those named above for $R^1$.

The radicals $R^{10}$ to $R^{17}$ and $R^{30}$ to $R^{33}$ are, independently of each other, hydrogen or a hydrocarbon group. The hydrocarbon groups can be linear or branched alkyl groups, cycloalkyl groups, aryl groups, alkyaryl groups or arylalkyl groups, and combinations of the above-named possibilities are also to be considered. The hydrocarbon groups can be inter-linked to form saturated and unsaturated cycles, five- and six-membered rings being preferred. Particularly preferred is linking to form benzene nuclei and incorporation of the group structure. Particularly preferably, the radicals $R^{10}$ to $R^{17}$ and $R^{30}$ to $R^{33}$ are however free from hetero atoms. In a further aspect, several of $R^{10}$ to $R^{17}$ and $R^{30}$ to $R^{33}$ equal hydrogen, for example all radicals $R^{10}$ to $R^{17}$ and $R^{30}$ to $R^{33}$ equal hydrogen.

The term nitrogen-containing compound covers the nitrogen-containing compounds which are capable of ammonium salt formation, i.e. quaternization. However, the presence of purely quarternary compounds or groups, e.g. tetramethylammonium or N-methylimidazolium salts or groups, is not ruled out.

Preferably, the nitrogen-containing compound to which all the following remarks relate is not $NH_3$. This is not intended to mean that $NH_3$ must preferably not be contained in component (b) or that generally the reaction preferably has to take place in the absence of $NH_3$, but only that, if $NH_3$ should be present, $NH_3$ is preferably not the only nitrogen-containing compound according to the following statements.

The nitrogen-containing compound can be an ammonium salt (in the conventional meaning of the term), i.e. it contains one or more no longer basic groups (e.g. several nitrogen atoms can be quaternized in a polyamine), provided the nitrogen-containing compound fulfils the necessarily prescribed conditions. This ammonium group can be derived from an organic or a mineral acid. For simplicity's sake, reference is not always made expressly to these salts in the following.

Preferred nitrogen-containing compounds (b) are those known as curing agents or accelerators in the state of the art. Usually, amines or imidazoles are used, but polyamines, ureas, triazines, triazoles, triazones, pyrimidines, thiodiazoles and similar heterocycles as well as derivatives of same are also suitable as nitrogen-containing compounds. Examples of nitrogen-containing compounds are tetramethylethylene diamine, dimethyloctylamine, dimethylaminoethanol, dimethylbenzylamine, 2,4,6-tris(dimethylaminomethyl)-phenol, N,N'-tetramethyldiaminodiphenylmethane, N,N'-dimethylpiperazine, N-methylmorpholine, N-methylpiperidine, N-ethylpyrrolidine, 1,4-diazabicyclo[2.2.2]-octane and quinolines. Suitable imidazoles are for example 1-methylimidazole, 2-methylimidazole, 1,2-dimethylimidazole, 1,2,4,5-tetramethylimidazole, 2-ethyl-4-methylimidazole, 1-cyanoethyl-2-phenylimidazole and 1-(4,6-diamino-s-triazinyl-2-ethyl-)-2-phenyl-imidazole. Of these, 1-methylimidazole and dimethylbenzylamine are particularly preferred.

Preferred aliphatic amines are those amines which are derived from the group $NR^2R^3_1$ the radicals $R^2$ and $R^3$ having the meaning given above.

In the following, possible versions of the process according to the invention for reaction of the phosphorus-containing component (a) with component (b) are explained:

X) Reaction of Ring-closed Phosphorus-containing Component (a) with Component (b) which has no Nitrogen-containing Compound with Basic NH-function In a first version, the phosphorus-containing component (a) is in its ring-closed form. This means for example that the version concerns i) a derivative of the intramolecular ester of 4-hydroxybutane-1 phosphinic acid or the intramolecular ester of 4-hydroxybutane-1-phosphinic acid (formulae X–XV) or ii) a derivative of the intramolecular anhydride of 2-hydroxycarbonyl-ethyl-phosphinic acid or the intramolecular anhydride of 2-hydroxy-carbonyl-ethyl-phosphinic acid (formulae XXX and XXXI). Should it be desired in this case to carry out the reaction with a nitrogen-containing compound which has no basic NH-function, it is necessary, in order to achieve the ring-opening of the phosphorus-containing component (a), to carry out the process according to the invention in such a way that it includes the reaction with at least one component (c), the component (c) being selected from water and mono- or polyhydric hydroxy compounds. The process need not be carried out so that the component (a) is first reacted with component (c). It is also possible to mix component (b) and (c) and then to add them to component (a), and it is equally possible to mix component (a) and component (b) and then add component (c). Preferred mono- or polyhydric hydroxy compounds are the mono- or polyhydric hydroxy compounds already mentioned in the section "latent ammonium salts", preferably the named aliphatic mono- or polyhydric aliphatic alcohols and mono- or polyhydric phenols.

It is possible that the ring-opening of the ring-closed form of component (a) takes place accompanied by reaction of component (a) with component (c). If, for example, component (a) i) is derived from the ring-closed form of 4-hydroxy-butane-1-phosphinic acid, etherification may occur through the reaction with a mono- or polyhydric hydroxy compound, a butanephosphinic acid etherified in 4-position being able to be formed for example. If component (a) ii) is derived from the ring-closed form of 2-hydroxycarbonyl-ethyl-phosphinic acid, esterification of the carboxylic acid group may occur for example, as a result of which an ethylphosphinic acid can be formed which is functionalized in 2-position with carboxylic acid ester.

If the hydroxy compound is a polyhydric hydroxy compound, the linking of several phosphinic acid groups may occur.

Y) Reaction of Ring-closed Phosphorus-containing Component (a) with Component (b) which Comprises a Nitrogen-containing Compound which has at least One Basic NH-function If component (a) is present in the ring-closed form then the process according to the invention can be carried out in such a way that a reaction is achieved accompanied by ring-opening if component (b) comprises a nitrogen-containing compound which has at least one basic NH function. However, one (or more) nitrogen-containing compound(s) which has (have) no NH function can of course also be used.

Z) Reaction of Ring-open Phosphorus-containing Component (a) with Component (b) which Comprises a Nitrogen-containing Compound If the phosphorus-containing component (a) is present in the ring-open form (formulae XVI–XXI, XXXII and XXXIII), then the process according to the invention consists of the reaction of component (a) with a component (b), component (b) comprising a nitrogen-containing compound.

The process according to the invention for preparing a latent combination compound or a latent ammonium salt is preferably carried out according to the versions Y) and Z) in such a way that it comprises the reaction with at least one component (c) (which is necessarily prescribed in version X), component (c) containing at least one compound selected from water and mono- or polyhydric hydroxy compounds.

IV. The Processes According to the invention

In the following discussion of the processes according to the invention, the term "molar" refers to mol equivalents. This means for example for the mono- or polyhydric hydroxy compound (and the same applies to the nitrogen-containing compound) that a mol equivalent is $1/n^{th}$ of the amount of substance of n-hydric hydroxy compound.

The processes according to the invention, i.e. the process of hydrolysis of the latent combination compound and the reaction of components (a), (b) and optionally (c) are not restricted to molar reactions. For example, it may be desired to hydrolyze the latent combination compound only with a sub-molar amount of reagent, which could produce a mixture of latent combination compound and latent ammonium salt. It may also be desired to carry out the process according to the invention of the reaction of at least one phosphorus-containing component (a) with at least one nitrogen-containing component (b), and optionally component (c), with a molar shortfall of component (b), relative to component (a), or to carry out the process with a molar excess of component (b), relative to component (a).

In a particularly preferred version, component (a), component (b) and optionally component (c) are reacted in a molar ratio, i.e. added in any sequence to one another.

The processes according to the invention can usually be described by a chemical reaction equation, selected reactions are shown in diagrams 1–3. When carrying out the processes, it is possible that in superimposed reactions, further rearrangements of the latent combination compounds or ammonium salts according to the invention take place. Such a superimposed reaction can proceed for example accompanied by formal splitting-off of water, e.g. this splitting-off of water can be intramolecular or intermolecular and go back to esterification, etherification, anhydride formation, amide formation etc. One example is the dehydration reaction proceeding in diagram 1 from 1-I to 1-III, which has already been described. This reaction water can intervene in the process according to the invention, in diagram 1 this is shown taking as an example the hydrolysis of 1-I to 1-IIa. The multitude of such possible superimposed reactions can lead to mixtures of latent combination compounds and latent ammonium salts (as well as optionally further compounds). Mixtures can also form if no molar reaction takes place in the selected process according to the invention. Mixtures can achieve the object forming the basis of this invention, as the present invention does expressly not exclude further compounds in addition to the latent combination compounds and latent ammonium salts according to the invention. The term "compound" as used in the description of this invention also includes these mixtures.

V. Use of the Latent Combination Compounds and Latent Ammonium Salts according to the Invention The invention relates furthermore to the use of the latent combination compounds and latent ammonium salts according to the invention in single-component epoxide resin systems for the preparation of coatings and moulded bodies. For example, the substances and substance mixtures are used in storage-stable, heat-curing single-component epoxide resin adhesives. Furthermore, the invention relates to products which have been manufactured using the above-named substances. As examples of such products, there may be cited:

prepregs and composite materials based on inorganic or organic reinforcing materials in the form of fibres, fleeces or fabrics, or on fabrics;

printed wiring boards made from glass-fibre fabric and epoxide resin systems;

moulded bodies of all kinds;

products with coatings made of epoxide resin; and bondings of various substrates, e.g. metal bondings in the design sector of automobile manufacture.

In addition to the epoxide resin component listed later, the epoxide resin system can furthermore comprise a solvent (thinning agent). This solvent (thinning agent) can originate in the preparation of the latent combination compound according to the invention or the latent ammonium salt according to the invention, for example if these were prepared by a process according to the invention. The process according to the invention was then carried out in this solvent. However, the solvent (thinning agent) can also be introduced into the epoxide resin system later.

Exemplary solvents are aprotic and preferably have a polar character. Examples are: N-methylpyrrolidone; dimethylformamide; ethers such as diethyl ether, tetrahydrofuran, dioxane, ethylene glycol-mono- or diether, propylene glycol-mono- or diether, butylene glycol-mono- or diether of monoalcohols with an optionally branched alkyl radical of 1 to 6 carbon atoms; ketones, such as for example acetone, methyl ethyl ketone, methyl isopropyl ketone, methyl isobutyl ketone, cyclohexanone and similar; esters, such as ethyl acetate, butyl acetate, ethyl glycol acetate, methoxypropyl acetate; halogenated hydrocarbons; but (cyclo)aliphatic and/or aromatic hydrocarbons, such as hexane, heptane, cyclohexane, toluene, the various xylenes and also aromatic solvents are also possible. The solvents can be used individually or in a mixture.

The latent combination compounds and latent ammonium salts according to the invention (compounds according to the invention) can be added as a reactive constituent to mixtures based on epoxide resin compounds and in this way be used for the latent curing/acceleration and flame-proofing of the cross-linked epoxide material. The amount used of the compounds according to the invention can vary within wide limits, in general 0.1 to 100 parts by weight are used, relative to 100 parts by weight of epoxide resin, preferably 0.5 to 30 parts. It is known that for particular applications, e.g. printed wiring boards, up to 30 weight-% flame-protection agent are required in order to achieve the corresponding specifications. The most favourable amount of latent combination compounds and latent ammonium salts in the respective epoxide resin system depends for example on the nature of the epoxide resin and on the type and presence of other components—including flame-protection agents and co-curing agents/accelerators—and can be easily and swiftly fixed in the individual case by the person skilled in the art by a few experiments, the epoxide resin system being able to have a broad or also a very specific potential for use.

There come into consideration as epoxide resin components almost all known compounds which on average have more than one 1,2-epoxide group in the molecule. Such resins can have an aliphatic, aromatic, cycloaliphatic, arylaliphatic or heterocyclic structure; they contain epoxide groups as side groups, or these groups form a part of an alicyclic or heterocyclic ring system. Epoxide resins of these types are generally known and available in the trade. As examples of epoxide resins of this type, there are to be mentioned:

I) Polyglycidyl and poly-(β-methylglycidyl) esters obtainable by reacting a compound with at least two carboxyl groups in the molecule and epichlorohydrin or glycerol dichlorohydrin or β-methylepichlorohydrin.
II) Polyglycidyl or poly-(β-methylglycidyl) ethers obtainable by reacting a compound with at least 2 free alcoholic hydroxy groups and/or phenolic hydroxy groups and a suitably substituted epichlorohydrin under alkaline conditions, or in the presence of an acidic catalyst and subsequent alkaline treatment.
III) Poly-(N-glycidyl) compounds.
IV) Poly-(S-glycidyl) compounds.
V) Epoxide compounds in which the epoxide groups form a part of an alicyclic or heterocyclic ring system.

Mixtures of epoxide resins can of course also be used.

The invention also relates to compositions which contain a latent combination compound or a latent ammonium salt together with an epoxide resin, and compositions which contain a pre-extended epoxide resin based on one of the compounds according to the invention. (Pre-extended epoxide resins are pre-reacted adducts containing still-free epoxide groups, of one or more epoxide resins with one or more compounds which contain at least two functional groups per molecule which react with epoxide groups.)

The compositions according to the invention can in addition contain further usual additives and modification agents in a quantity suitable for the respective purpose, such as for example heat stabilizers, light stabilizers, UV absorbers, antioxidants, antistatic agents, preservatives, adhesion promoters, fillers, pigments, lubricants, foaming agents, fungicides, plasticizers, processing auxiliaries, further flame-retarding additives, further curing agents/accelerators and means of reducing smoke development.

In a preferred version, the epoxide resin system is processed in a resin-injection process. The sufficient processing stability needed for this at average temperatures and short curing time at higher temperatures become possible thanks to the latent combination compounds according to the invention and latent ammonium salts of this invention. In addition, the possibility of comparatively low curing temperatures also makes the systems attractive for the efficient processing of adhesives.

The latent combination compounds and latent ammonium salts obtainable through the present invention can be liquid and offer numerous processing advantages compared with the conventional curing agents which are solids. In particular, with the novel single-component epoxide resin systems, the problem of the separation of the curing agent/accelerator component from the resin during storage and/or curing can be overcome. Furthermore, the epoxide resin systems according to the invention can be easily processed in resin-injection systems at average temperatures whilst they cure completely at somewhat higher temperatures.

The epoxide resin system comprises at least one epoxide resin component and at least one of the latent combination compounds or latent ammonium salts according to the invention, the use of mixtures of latent combination compound and latent ammonium salt, with each other and/or with further constituents (e.g. the named additives and modification agents), in any ratio, being possible.

The epoxide resin systems obtainable through this invention have a defined curing temperature, which is achieved by a latency of the compounds according to the invention. The initiation temperature is set by chemical modification of the latent combination compounds and latent ammonium salts. In addition, the products which are prepared from the novel single-component resins obtainable through the invention are given flame-retarding properties.

VI. EXAMPLES

Example 1

A phosphorus-containing component (a) of the ring-closed formula XXX was used in which $R^{30}$ to $R^{33}$ equalled hydrogen and $R^{34}$ was methyl:

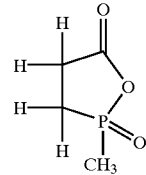

1-methylimidazole (N-methylimidazole) was chosen as component (b), and component (c) is methanol.

The reaction of components (a), (b) and (c) can take place in any order and results in all cases in 1-methylimidazolium (2-methoxy-carbonyl-ethyl) (methyl)-phosphinate. This latent ammonium salt according to the invention is liquid at room temperature. A mixture of 10 wt. % latent ammonium salt and 90 wt. % epoxide resin was prepared. The system is, regardless of the resin type, storage-stable at room temperature and does not cure for several hours even at 70° C., which illustrates its suitability for use in resin-injection processes.

At 125° C., a complete curing takes place within 15 minutes. The glass transition point $T_g$ (DSC, heating rate 10K/min) was determined:

(a) Using a DGEBA resin (e.g. Epikote 828), the $T_g$ is 120° C.
(b) Using an epoxidized Novolak resin (e.g. Rütapox 0300), the $T_g$ is 1700° C.

Example 2

A phosphorus-containing component (a) of the ring-closed formula XXX was used in which $R^{30}$ to $R^{33}$ equalled hydrogen and $R^{34}$ was methyl (cf. example 1). 1-methylimidazole (N-methylimidazole) was chosen as component (b), and component (c) is phenol.

The reaction of components (a), (b) and (c) can take place in any order and results in all cases in 1-methylimidazolium (2-phenoxycarbonyl-ethyl) (methyl)-phosphinate. This latent ammonium salt according to the invention is liquid at room temperature. A mixture of 10 wt. t latent ammonium salt and 90 wt. % epoxide resin was prepared. The epoxide resin system is, regardless of the resin type, storage-stable at room temperature and does not cure for several hours even at 70° C.

At 125° C., a complete curing takes place within 15 minutes. The glass transition point $T_g$ (DSC, heating rate 10K/min) was determined:

(a) Using a DGEBA resin (e.g. Epikote 828), the $T_g$ is 118° C.

(b) Using an epoxidized Novolak resin (e.g. Rütapox 0300), the $T_g$ is 190° C.

Example 3

A phosphorus-containing component (a) of the ring-closed formula XXX was used in which $R^{30}$ to $R^{33}$ equalled hydrogen and $R^{34}$ was methyl (cf. example 1). 1-methylimidazole (N-methylimidazole) was chosen as component (b), and component (c) is ethylene glycol.

The reaction of components (a), (b) and (c) can take place in any order and results in all cases in di-(1-methylimidazolium) salt of the bis-phosphinate linked by the dihydroxy compound ethylene glycol. The latent ammonium salt is represented in the following:

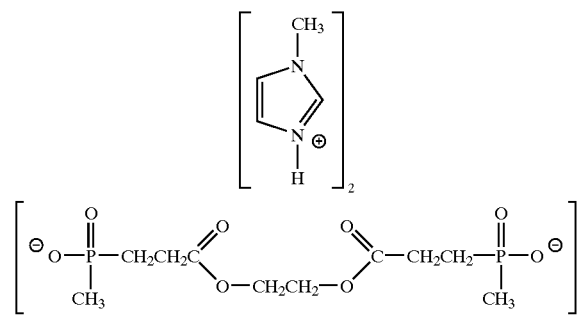

This latent ammonium salt according to the invention is also liquid at room temperature. A mixture of 10 wt. % of latent ammonium salt and 90 wt. % of epoxide resin was prepared. The epoxide resin system is, regardless of the resin type, storage-stable at room temperature and does not cure for several hours even at 70° C.

At 125° C., a complete curing takes place within 15 minutes. The glass transition point $T_g$ (DSC, heating rate 10K/min) was determined:

(a) Using a DGEBA resin (e.g. Epikote 828), the $T_g$ is 137° C. (b) Using an epoxidized Novolak resin (e.g. Rütapox 0300), the $T_g$ is 180° C.

In the following, diagrams 1 to 3, to which reference was made, are shown:

FIG. 1

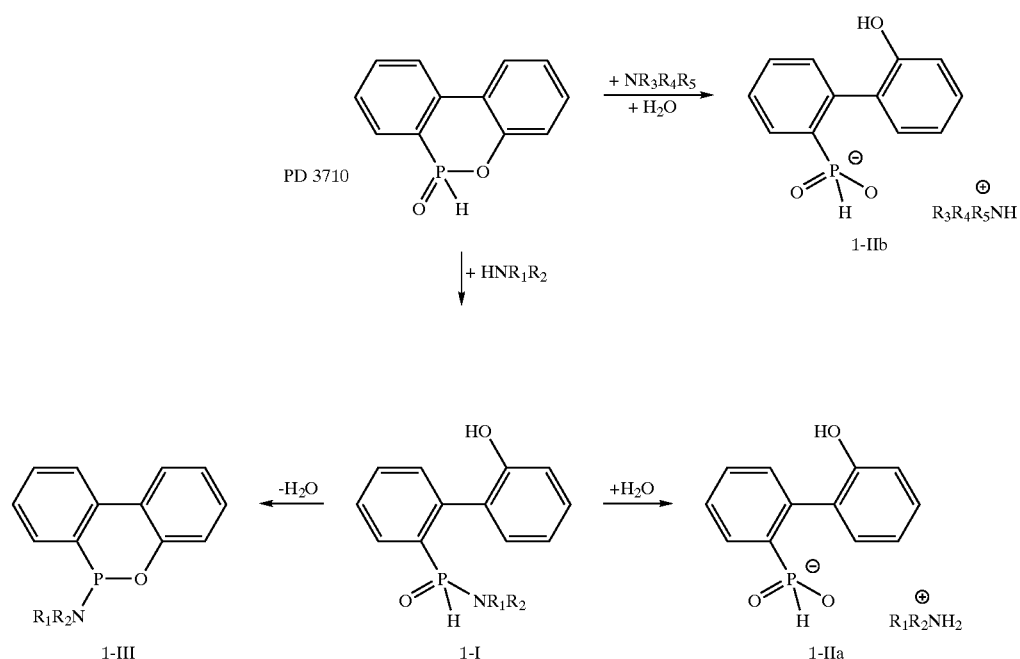

FIG. 3
Oxa-phosphalan

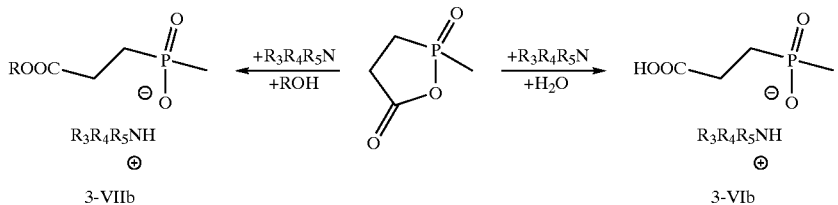

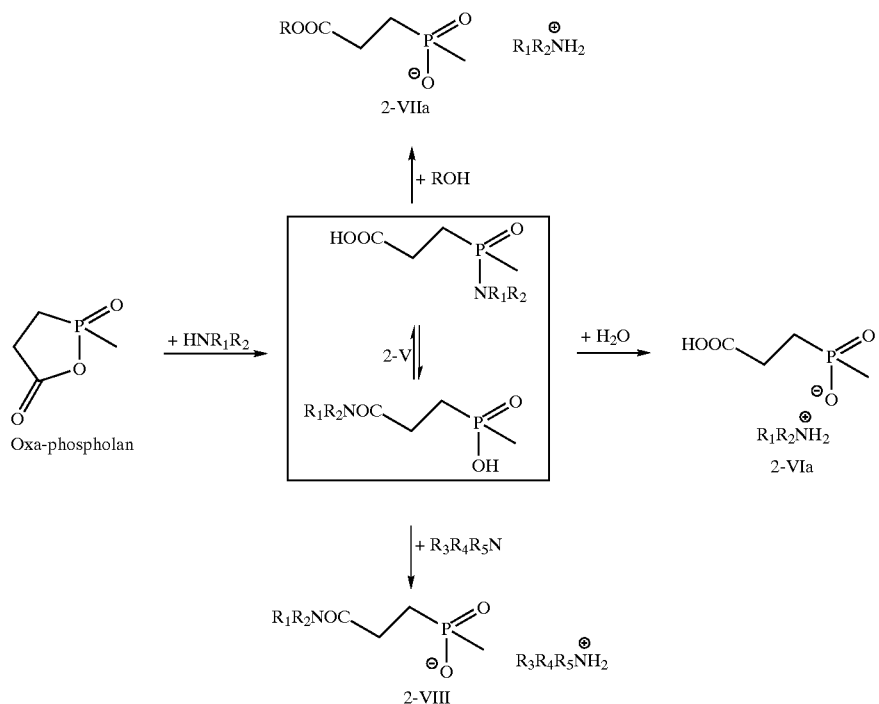

FIG. 2

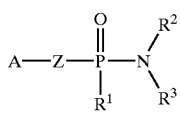

Oxa-phospholan

What is claimed is:

1. Latent combination compound according to formula I $$A-Z-\overset{\overset{O}{\|}}{\underset{R^1}{P}}-N\overset{R^2}{\underset{R^3}{}}$$

I in which $R^1$ equals a general radical $R^0$, $R^0$ being hydrogen or a linear or branched, saturated or unsaturated hydrocarbon group with 1 to 100 carbon atoms, which can optionally contain one or more heteroatoms selected from the group consisting of oxygen, nitrogen, sulphur, phosphorus, silicon and halogen, wherein in $NR^2R^3$, the $R^2$ and $R^3$ groups are linked and are derived from imidazole, 2-methyl imidazole, 2-ethyl-4-methylimidazole, or 1-methyl imidazole, A being selected from the group consisting of OH and COX in which X is selected from the group consisting of OH, $NH_2$, $NHR^a$, a $NR^bR^c$ and $O^-M^+$, with $R^a$ to $R^c$, independently of each other, having the meaning given for $R^0$, and $R^b$ and $R^c$ being able to be linked accompanied by the formation of a cycle or several cycles and $M^+$ being any metal ion, and Z denoting a divalent linear or branched, saturated or unsaturated hydrocarbon chain with 2 to 100 carbon atoms, which can optionally contain one or more cycles and can optionally contain one or more heteroatoms selected from the group consisting of oxygen, nitrogen, sulphur, phosphorus, silicon and halogen.

2. Latent combination compound according to claim 1, wherein $R^1$ is different from A—Z.

3. Latent combination compound according to claim 1 wherein $R^1$ is selected from hydrogen, methyl and hydrocarbon groups which have at least one epoxy function.

4. Latent combination compound according to claim 1, wherein Z does not comprise heteroatoms in the hydrocarbon chain.

5. Latent combination compound according to claim 1, wherein a.) A equals OH and b.) Z has 4 carbon atoms in the chain.

6. Latent combination compound according to claim 1, wherein
a.) A equals COOH,
b.) $R^1$ equals methyl or hydrogen, and
c.) Z is linear or branched and is alkane-($\alpha$, $\beta$)-diyl or arylalkane-($\alpha$, $\beta$)-diyl.

7. Process for preparing a latent ammonium salt, wherein at least one latent combination compound according to formula I

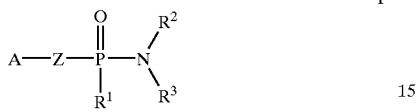

I in which $R^1$ equals a general radical $R^0$, $R^0$ being hydrogen or a linear or branched, saturated or unsaturated hydrocarbon group with 1 to 100 carbon atoms, which can optionally contain one or more heteroatoms selected from the group consisting of oxygen, nitrogen, sulphur, phosphorus, silicon and halogen, $R^2$ and $R^3$, independently of each other, having the meaning given for $R^0$, $R^2$ and $R^3$ being able to be linked accompanied by the formation of a cycle or several cycles, A being selected from the group consisting of OH and COX in which X is selected from the group consisting of OH, $NH_2$, $NHR^a$, $NR^bR^c$, and $O^-M^+$, with $R^a$ to $R^c$ independently of each other, having the meaning given for $R^0$, and $R^b$ and $R^c$ being able to be linked accompanied by the formation of a cycle or several cycles and $M^+$ being any metal ion, and Z denoting a divalent linear or branched, saturated or unsaturated hydrocarbon chain with 2 to 100 carbon atoms, which can optionally contain one or more cycles and can optionally contain one or more heteroatoms selected from the group consisting of oxygen, nitrogen, sulphur, phosphorus, silicon and halogen is reacted with at least one reagent which comprises water, resulting in the splitting of the P—N bond shown in formula I.

8. Latent ammonium salt, obtainable by the process according to claim 7.

9. Single-component epoxide resin system, comprising at least one epoxide resin component and at least one curing agent/accelerator component comprising the latent combination ammonium salts according to claim 8 as well as optionally further additives and modification agents.

10. Single-component epoxide resin adhesive, comprising at least one epoxide resin component and at least one curing agent/accelerator component comprising the latent ammonium salts according to claim 8 as well as optionally further additives and modification agents.

11. Process for preparing a latent ammonium salt, wherein at least one latent combination compound according to formula I

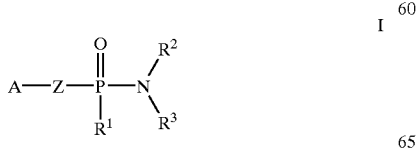

I in which $R^1$ equals a general radical $R^0$, $R^0$ being hydrogen or a linear or branched, saturated or unsaturated hydrocarbon group with 1 to 100 carbon atoms, which can optionally contain one or more heteroatoms selected from the group consisting of oxygen, nitrogen, sulphur, phosphorus, silicon and halogen, $R^2$ and $R^3$, independently of each other, having the meaning given for $R^0$, $R^2$ and $R^3$ being able to be linked accompanied by the formation of a cycle or several cycles, Z denoting a divalent linear or branched, saturated or unsaturated hydrocarbon chain with 2 to 100 carbon atoms, which can optionally contain one or more cycles and can optionally contain one or more heteroatoms selected from the group consisting of oxygen, nitrogen, sulphur, phosphorus, silicon and halogen, in which A equals COOH, is reacted with at least one reagent which comprises at least one compound selected from water, and mono- or polyhydric hydroxy compounds, resulting in the splitting of the P—N bond shown in formula I.

12. Process according to claim 11, wherein the hydroxy compound is selected from mono- or polyhydric phenols and mono- or polyhydric alcohols.

13. Process according to claim 11, including the esterification of the group A by a mono- or polyhydric hydroxy compound.

14. Process for preparing a latent combination compound or a latent ammonium salt, wherein at least one phosphorus-containing component (a) selected from
i) derivatives of the intramolecular ester of 4-hydroxy-butane-1 phosphinic acid according to one of the ring-closed formulae X to XV

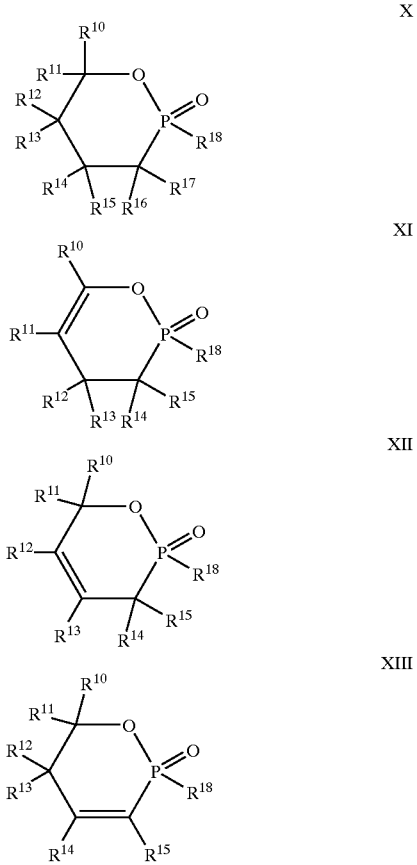

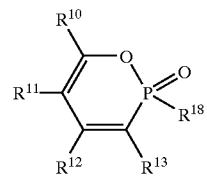

XIV

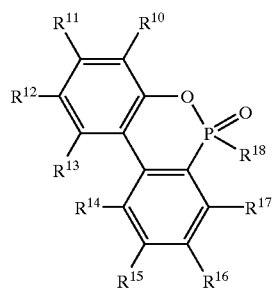

XV in which $R^{10}$ to $R^{18}$, independently of each other, have the general meaning given for $R^0$ wherein $R^0$ is hydrogen or a linear or branched, saturated or unsaturated hydrocarbon group with 1 to 100 carbon atoms, which can optionally contain one or more heteroatoms selected from the group consisting of oxygen, nitrogen, sulphur, phosphorus, silicon and halogen; and two or more of $R^{10}$ to $R^{17}$ being able to be linked accompanied by the formation of a cycle or several cycles, and ii) derivatives of phospholan according to one of the ring-closed formulae XXX and XXXI

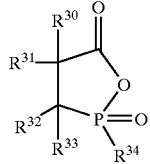

XXX

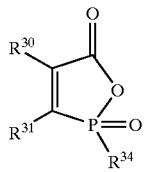

XXXI in which $R^{30}$ to $R^{34}$, independently of each ocher, have the general meaning given for $R^0$ above and one or more of $R^{30}$ to $R^{33}$ are able to be linked accompanied by the formation of a cycle or several cycles, is reacted with a component (b) which comprises a nitrogen-containing compound which has no basic NH function, the process comprising the reaction with at least one component (c) selected from water and mono- or polyhydric hydroxy compounds.

15. Process according to claim 14, wherein $R^{10}$ to $R^{17}$ and $R^{30}$ to $R^{33}$, independently of each other, are selected from hydrogen and linear or branched aliphatic hydrocarbon groups.

16. Process according to claim 14, wherein $R^{18}$ and $R^{34}$, independently of each other, are selected from the group consisting of hydrogen, methyl and hydrocarbon groups which have at least one epoxy function.

17. Process according to claim 14, wherein $R^{30}$ to $R^{33}$ are hydrogen in the phospholan of the formulae XXX to XXXIII and $R^{34}$ is methyl.

18. Process according to claim 14, wherein the mono- or polyhydric hydroxy compound is selected from mono- or polyhydric phenols and mono- or polyhydric alcohols.

19. Process according to claim 14, wherein the nitrogen-containing compound is selected from the group consisting of tetramethylethylene diamine, dimethyloctylamine, dimethylaminoethanol, dimethylbenzylamine, 2,4,6-tris(dimethylaminomethyl)-phenol, N,N'-tetramethyldiaminodiphenylmethane, N,N'-dimethylpiperazine, N-methylmorpholine, N-methylpiperidine, N-ethylpyrrolidine, 1,4-diazabicyclo[2.2.2]-octane, quinolines, 1-methylimidazole, 1,2-dimethylimidazole, 1,2,4,5-tetramethylimidazole, 1-cyanoethyl-2-phenylimidazole and 1-(4,6-diamino-s-triazinyl-2-ethyl-)-2-phenylimidazole as well as their salts.

20. Latent combination compound or latent ammonium salt, obtainable by the process according to claim 14.

21. Process for preparing a latent combination compound or a latent ammonium salt, wherein at least one phosphorus-containing component (a) selected from i) derivatives of the intramolecular ester of 4-hydroxy-butane-1 phosphinic acid according to one of the ring-closed formulae X to XV

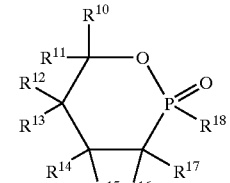

X

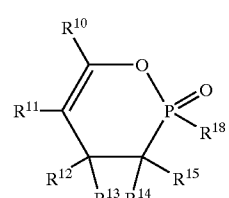

XI

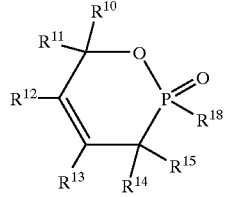

XII

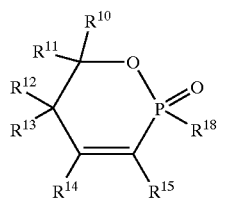

XIII

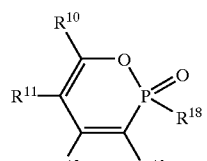

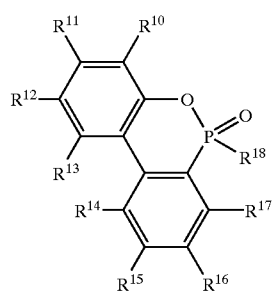

in which $R^{10}$ to $R^{18}$, independently of each other, have the general meaning given for $R^0$,
wherein $R^0$ is hydrogen or a linear or branched, saturated or unsaturated hydrocarbon group with 1 to 100 carbon atoms, which can optionally contain one or more heteroatoms selected from the group consisting of oxygen, nitrogen, sulphur, phosphorus, silicon and halogen; and
two or more of $R^{10}$ to $R^{17}$ being able to be linked accompanied by the formation of a cycle or several cycles, and ii) derivatives of phospholan according to one of the ring-closed formulae XXX and XXXI

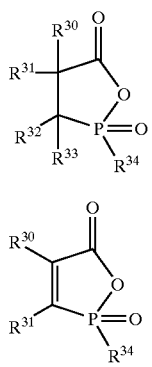

in which $R^{30}$ to $R^{34}$, independently of each other, have the general meaning given for $R^0$ above and one or more of $R^{30}$ to $R^{33}$ can be linked accompanied by the formation of a cycle or several cycles,
is reacted with a component (b) which comprises a nitrogen-containing compound which has at least one basic NH function.

22. Process according to claim 16, comprising the reaction with at least one reagent selected from water and mono- or polyhydric hydroxy compounds.

23. Process according to claim 21, wherein the nitrogen-containing compound is selected from the group consisting of imidazole, 2-methylimidazole and 2-ethyl-4-methylimidazole as well as their salts.

24. Single-component epoxide resin system, comprising at least one epoxide resin component and at least one curing agent/accelerator component comprising the latent combination compounds according to formula I

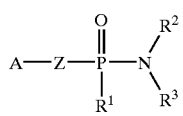

in which $R^1$ equals a general radical $R^0$,
$R^0$ being hydrogen or a linear or branched, saturated or unsaturated hydrocarbon group with 1 to 100 carbon atoms, which can optionally contain one or more heteroatoms selected from the group consisting of oxygen, nitrogen, sulphur, phosphorus, silicon and halogen,
$R^2$ and $R^3$, independently of each other, having the meaning given for $R^0$, $R^2$ and $R^3$ being able to be linked accompanied by the formation of a cycle or several cycles,
A being selected from the group consisting of OH and COX in which X is selected from the group consisting of OH, $NH_2$, $NHR^a$, $NR^bR^c$, and $O^-M^+$, $R^a$ to $R^c$ independently of each other, having the meaning given for $R^0$, and $R^b$ and $R^c$ being able to be linked accompanied by the formation of a cycle or several cycles and $M^+$ being any metal ion, and
Z denoting a divalent linear or branched, saturated or unsaturated hydrocarbon chain with 2 to 100 carbon atoms, which can optionally contain one or more cycles and can optionally contain one or more heteroatoms selected from the group consisting of oxygen, nitrogen, sulphur, phosphorus, silicon and halogen,
as well as optionally further additives and modification agents.

25. Prepregs, comprising an inorganic or organic reinforcing material in the form of fibres, a fleece, fabric or flat material which is impregnated with a single-component epoxide resin system according to claim 24.

26. Process for preparing fibre-reinforced composite materials with flame-retarding properties, comprising
the curing of a prepreg according to claim 25 at a temperature between 70° C. and 160° C.

27. Fibre-reinforced composite material with flame-retarding properties, wherein said material is the cured form of a prepreg according to claim 25.

28. Printed wiring boards made of prepregs, wherein their structure comprises at least one composite material according to claim 27.

29. Process for preparing moulded bodies, coatings and bondings with flame-retarding properties, wherein the single-component epoxide resin system according to claim 24 is cured.

30. Moulded bodies, coatings and bondings with flame-retarding properties obtainable by curing from a single-component epoxide resin system according to claim 24.

31. Resin-injection process for fibre-reinforced composite materials with flame-retarding properties, comprising
a.) the impregnation of an inorganic or organic reinforcing material in the form of fibres, a fleece, fabric or flat material with a single-component epoxide resin system according to claim 27 and
b.) the curing of the impregnated reinforcing material at a temperature between 70° C. and 160° C.

32. Single-component epoxide resin adhesive, comprising
at least one epoxide resin component and at least one curing agent/accelerator component comprising the latent combination compounds according to formula I

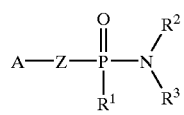

in which $R^1$ equals a general radical $R^0$, $R^0$ being hydrogen or a linear or branched, saturated or unsaturated hydrocarbon group with 1 to 100 carbon atoms, which can optionally contain one or more heteroatoms selected from the group consisting of oxygen, nitrogen, sulphur, phosphorus, silicon and halogen, $R^2$ and $R^3$, independently of each other, having the meaning given for $R^0$, $R^2$ and $R^3$ being able to be linked accompanied by the formation of a cycle or several cycles, A being selected from the group consisting of OH and COX in which X is selected from the group consisting of OH, $NH_2$, $NHR^a$, $NR^bR^c$, and $O^-M^+$, with $R^a$ to $R^c$ independently of each other, having the meaning given for $R^0$, and $R^b$ and $R^c$ being able to be linked accompanied by the formation of a cycle or several cycles and $M^+$ being any metal ion, and Z denoting a divalent linear or branched, saturated or unsaturated hydrocarbon chain with 2 to 100 carbon atoms, which can optionally contain one or more cycles and can optionally contain one or more heteroatoms selected from the group consisting of oxygen, nitrogen, sulphur, phosphorus, silicon and halogen, as well as optionally further additives and modification agents.

33. Process for preparing moulded bodies, coatings and bondings with flame-retarding properties, wherein the single-component epoxide resin adhesive according to claim 32 is cured.

34. Moulded bodies, coatings and bondings with flame-retarding properties obtainable by curing from a single-component epoxide resin adhesive according to claim 32.

35. Process for preparing a latent combination compound or a latent ammonium salt, wherein at least one phosphorus-containing component (a) selected from i) derivatives of 4-hydroxy-butane-1 phosphinic acid according to one of the ring-open formulae XVI to XXI

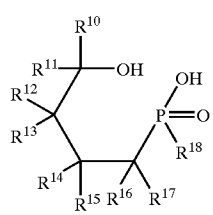

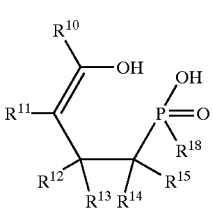

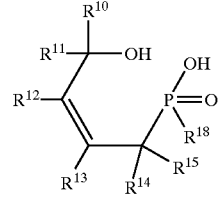

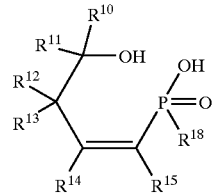

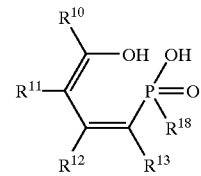

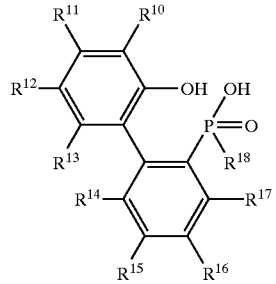

in which $R^{10}$ to $R^{18}$, independently of each other, have the general meaning given for $R^0$, wherein $R^0$ is hydrogen or a linear or branched, saturated or unsaturated hydrocarbon group with 1 to 100 carbon atoms, which can optionally contain one or more heteroatoms selected from the group consisting of oxygen, nitrogen, sulphur, phosphorus, silicon and halogen; and two or more of $R^{10}$ to $R^{17}$ being able to be linked accompanied by the formation of a cycle or several cycles, and ii) derivatives of phospholan according to one of the ring-open formulae XXXII and XXIII

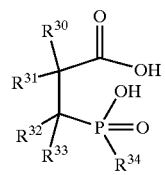

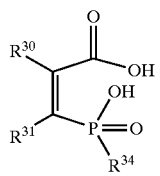
XXXIII
in which $R^{30}$ to $R^{34}$, independently of each other, have the general meaning given for $R^0$ above, and one or more of $R^{30}$ to $R^{33}$ can be linked accompanied by the formation of a cycle or several cycles,
is reacted with a component (b) which comprises a nitrogen-containing compound.
* * * * *